United States Patent [19]

Wilson et al.

[11] 4,209,434
[45] Jun. 24, 1980

[54] DENTAL CEMENT CONTAINING POLY(CARBOXYLIC ACID), CHELATING AGENT AND GLASS CEMENT POWDER

[75] Inventors: Alan D. Wilson, Liphook; Stephen Crisp, Hounslow, both of England

[73] Assignee: National Research Development Corporation, England

[21] Appl. No.: 830,776

[22] Filed: Sep. 6, 1977

Related U.S. Application Data

[63] Continuation of Ser. No. 595,039, Jul. 11, 1975, abandoned, which is a continuation of Ser. No. 350,885, Apr. 13, 1973, abandoned.

[30] Foreign Application Priority Data

Apr. 18, 1972 [GB] United Kingdom ............... 17880/72

[51] Int. Cl.$^2$ .............................................. C08L 33/02
[52] U.S. Cl. ................................ 260/29.6 H; 106/35; 260/29.6 M; 260/29.6 E; 260/29.6 N; 260/29.6 B; 260/29.6 WB; 260/42.43; 525/4; 525/5; 525/6; 526/303; 526/317
[58] Field of Search .................... 260/29.6 M, 29.6 H, 260/29.6 E, 29.6 N, 29.6 R, 29.6 WB; 106/35; 526/303, 317, 4, 5, 6

[56] References Cited

U.S. PATENT DOCUMENTS

| 3,655,605 | 4/1972 | Smith | 260/29.6 M |
| 3,741,926 | 6/1973 | Jurecic | 260/29.6 M |
| 3,751,391 | 8/1973 | Smith | 260/29.6 M |
| 3,804,794 | 4/1974 | Schmitt et al. | 260/29.6 M |
| 3,814,717 | 6/1974 | Wilson et al. | 260/29.6 M |
| 4,016,124 | 4/1977 | Crisp et al. | 260/29.6 H |
| 4,143,018 | 3/1979 | Crisp et al. | 260/29.6 H |

OTHER PUBLICATIONS

Advanced Organic Chemistry—Royals, 1954, pp. 28-29.

Primary Examiner—Harold D. Anderson
Attorney, Agent, or Firm—Jacobs & Jacobs

[57] ABSTRACT

A poly(carboxylate) cement pack comprising a water soluble poly(carboxylic acid) having a relative viscosity of from 1.05 to 2.00, a chelating agent and a cement powder which will react with the poly(carboxylic acid) in the presence of the chelating agent and water to give a plastic mass which rapidly hardens to form a poly(carboxylate) cement.

22 Claims, No Drawings

DENTAL CEMENT CONTAINING POLY(CARBOXYLIC ACID), CHELATING AGENT AND GLASS CEMENT POWDER

This is a continuation of Ser. No. 595,039 filed July 11, 1975, which in turn is a continuation of Ser. No. 350,885, filed Apr. 13, 1973, both now abandoned.

This invention relates to poly(carboxylate) cements and is particularly concerned with cements for use in dentistry.

The materials known as dental cements have many applications in dentistry including use as filling materials for restoring teeth and for cementing inlays and crowns into place in the tooth, providing a base and/or lining in a tooth cavity, providing a temporary fixing for the bonds of orthodontic appliances to the teeth and sealing root-canals after endodontic treatment. In recent years the traditional phosphate dental cements, i.e. zinc phosphate dental cement and dental silicate cement, have been to some extent displaced for many applications by the new "poly(carboxylate) dental cements", in which the cement-forming liquid is an aqueous solution of a poly(carboxylic acid). Such a cement is described and claimed in our British Pat. No. 1,139,430.

The poly(carboxylate) cements have improved acid and stain resistance over conventional dental cements and have the additional advantage that they do not irritate pulpal tissues. However, it has been found in practice that poly(carboxylate) cements occasionally have a slower hardening rate than conventional materials and an improvement in this respect would be desirable.

According to the present invention an improvement in the rate of hardening of a poly(carboxylate) cement is obtained by the addition thereto of a chelating agent.

In one aspect, therefore, the present invention provides a poly(carboxylate) cement pack comprising a water soluble poly(carboxylic acid) having a relative viscosity as hereinafter defined of from 1.05 to 2.00, a chelating agent and a cement powder which will react with the poly(carboxylic acid) in the presence of the chelating agent and water to give a plastic mass which rapidly hardens to form a poly(carboxylate) cement.

The invention also provides a process for the production of a poly(carboxylate) cement which comprises mixing a water soluble poly(carboxylic acid) having a relative viscosity as hereinafter defined of from 1.05 to 2.00 with a cement powder in the presence of a chelating agent and water to give a plastic mass which rapidly hardens to form a poly(carboxylate) cement.

The invention further provides a cement-forming liquid for use as a component of a poly(carboxylate) cement which comprises an aqueous solution of a water soluble poly(carboxylic acid) having a relative viscosity as hereinafter defined of from 1.05 to 2.00 together with a chelating agent.

Poly(carboxylate) cement packs in accordance with this invention preferably comprise a poly(carboxylic acid) in the form of an aqueous solution containing from 20 to 65% by weight of the poly(carboxylic acid). The poly(carboxylate) cement pack may be a two part pack in which the weight ratio of powder to liquid in the two parts is preferably from 0.5:1 to 5:1 so that when the entire contents of the pack are mixed together a rapidly hardening cement is obtained. In another embodiment the pack may contain the powder and the liquid in separate capsules, the total amount of powder in the pack and the total amount of liquid in the pack being in the appropriate ratio. In a further embodiment, both components may be encapsulated in the same capsule, in the desired ratio, provided that steps are taken to prevent premature reaction. In a still further embodiment the pack may be a one part pack containing an intimately blended mixture of the cement powder, solid water-soluble poly(carboxylic acid) and chelating agent, the ratio of powder to poly(carboxylic acid) being from 1:1 to 10:1, the mixture requiring the addition of water to produce the cement. The mixed powder and the water may be contained in the same capsules provided steps are taken to prevent premature reaction, for example by dividing the capsule.

This latter procedure generally requires some form of mechanical mixing.

In the above mentioned embodiments the cement powder is from 15 to 85% by weight, the poly(carboxylic acid) is from 3 to 50% by weight, and the water is from 5 to 70% by weight of the total composition.

It is found that when the components are mixed together a plastic mass is obtained which sets rapidly in the mouth (1.5 to 10 minutes following completion of preparation).

The chelating agent is added to the poly(carboxylic acid) in an amount sufficient to obtain the desired working time and hardening rate. It is usually not necessary to add more than about 20% by weight of the chelating agent based upon the weight of the poly(carboxylic acid) and preferably the chelating agent is present in an amount of from 0.01 to 10% by weight, such as for example about 5% by weight, based on the weight of the poly(carboxylic acid). A wide range of chelating agents may be used in the present invention, particularly those containing chelating hydroxy or carboxyl groups or both, such as for example, ethylene diamine tetraacetic acid, salicylic acid, citric acid, 2,4 and 2,6-dihydroxybenzoic acids, dihydroxy tartaric acid, nitrilotriacetic acid, tartaric acid, mellitic acids and polyglycols. Excellent results have been obtained using 5% by weight of tartaric or citric acid. Alternatively, the chelating agent may be added in the form of a metal chelate, particularly a di- or tri-valent metal chelate. Examples of especially suitable metal chelates include complexes of $\beta$-diketones with aluminium and chromium, for example aluminium and chromium triacetylacetonates, and ethylene diamine tetraacetic acid complexes of zinc and copper. The poly(carboxylic acid) does not function as a chelating agent in this invention.

The water solube poly(carboxylic acid) has a relative viscosity as hereinafter defined of from 1.05 to 2.0, and it is generally found that the above relative viscosity range corresponds to an average molecular weight of from 1500 to 150,000 when determined by the method of Sakamoto (Chemical Abstract 58 13160c). In this specification relative viscosity is defined as the viscosity measured with a capillary viscometer of a 1% by weight to volume solution of the poly(carboxylic acid) in twice molar sodium hydroxide solution at 25° C. relative to the viscosity of the twice molar sodium hydroxide solution.

The preferred poly(carboxylic acids) are those prepared by the homo-polymerisation and co-polymerisation of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid and tiglicinic acid. Suitable monomers for copolymerising with the unsaturated aliphatic carboxylic acids include unsaturated aliphatic compounds such as for example acrylamide, acrylonitrile, vinyl chloride, allyl chloride, vinyl acetate, and 2-hydroxyethyl methacrylate. Ter- and higher polymers may be used if desired. Particularly preferred are the homopolymers and co-polymers of acrylic acid. For dental applications the poly(carboxylic acid) should be surgically acceptable, that is to say, it should be substantially free from unpolymerised monomers and other undesirable components. Although poly (carboxylic acids) having a relative viscosity of from 1.05 to 2.0 are readily water soluble, the choice of concentration and molecular weight should be such as to make a solution which is not too viscous since otherwise "cobwebbing" may become a problem when the desired quantity of solution is removed from its container and mixed with the cement powder. For good cement formation a preferred concentration range is from 40 to 65% by weight and a preferred relative viscosity range is from 1.10 to 1.60. Particularly preferred cements may be produced using from 44 to 55% concentrations of a poly (carboxylic acid) with a relative viscosity of from 1.20 to 1.30. It is noteworthy, when selecting suitable combinations of concentration and molecular weight, that stronger solutions of any particular polymer are more difficult to mix and weaker solutions give lower cement strengths.

Poly(carboxylic acid) solutions have a tendency to gel on standing for several months, and this may be minimised by the addition of suitable stabilising agents to the liquid. Concentrations of up to about 20% by weight based on the weight of the poly(carboxylic acid) and preferably from 0.1 to 10% by weight of the stabilising agent may be used as desired. Suitable stabilising agents include those compounds which are capable of disrupting the structure of hydrogen bonded liquids. These compounds are usually either proton acceptors, or compounds containing chaotropic or structure breaking ions. Examples of suitable proton acceptors include ketones, for example, acetone, butan-2-one and acetylacetone; alcohols, for example, methanol, propan-2-ol and t-butyl alcohol; glycols, for example ethylene glycol and polyglycols;ureas for example urea and thiourea; and amines for example ethanolamine. Examples of suitable chaotropic or structure breaking ions include the perchlorate ion and then hexametaphosphate ion. Alternatively or in addition to the stabilising agent the poly(carboxylic acid) solution may be subjected to a thermal treatment in which it is heated to a temperature from 60° to 100° C. for a period of up to about 1 hour. Certain stabilising agents, for example polyglycols, can also act as chelating agents.

The poly(carboxylic acid) is mixed with a cement powder to form a plastic mass which sets rapidly in the mouth (1.5 to 10 mins. following completion of preparation). The cement powder, which is an ion-leachable powder which can react with a poly(carboxylic acid) in the presence of water, may for example comprise a simple metal oxide, preferably one that has been deactivated by heat treatment, for example zinc oxide to which there may be added up to about 10% by weight of other metal oxides such as for example magnesium oxide. Alternatively, the cement powder may comprise a fused oxide, made by heating a mixture of simple oxides to fusion temperature, or an oxide glass, for example one comprising calcium or sodium oxide with alumina, silica and phosphorus pentoxide. Most preferably, however, the cement powder comprises a fluoroaluminosilicate glass powder as described and claimed in our co-pending British application No. 61041/69, now British Pat. No. 316,129, wherein the ratio by weight of silica to alumina is from 1.5 to 2.0 and the ratio by weight of fluorine to alumina is from 0.6:2.5, or wherein the ratio by weight of silica to alumina is from 0.5:1.5 and the ratio by weight of fluorine to alumina is from 0.25:2.0. The fluoroaluminosilicate glasses may be prepared by fusing mixtures of silica ($SiO_2$) alumina ($Al_2O_3$), cryolite ($Na_3AlF_6$) and fluorite ($CaF_2$) in the appropriate proportions at a temperature above 950° C. Suitable methods for preparing the glasses are described in the aforementioned co-pending Application.

Fluorides, bacteriostatic agents or antibiotics may be added to the cement powder in minor amounts as desired to provide some antibacterial or anticariogenic action.

The degree of fineness of the cement powder should preferably be such that it produces a smooth cement paste which sets within a clinically acceptable period when mixed with the poly(carboxylic acid) liquid and the chelating agent. Preferably the degree of fineness of the powder is such that it will pass through a 150 mesh BS. sieve, and most preferably such that it passes through a 350 mesh BS. sieve.

In dental applications, the cements of this invention are designed to be made by the practitioner immediately prior to use as in the conventional manner. Thus, the materials in the one or two part pack are brought together and mixed forming a plastic mass which can be cast, moulded or otherwise formed into the required shape during the brief period in which the mixture retains its plastic properties. For example, a quantity of poly(carboxylic acid) solution sufficient to make up one small batch of cement may be easily withdrawn from its container using a dental spatula or similar instrument or extruded from a tube or like container and this may be mixed with a quantity of a dental cement powder on a suitable surface. The components can be mixed quite rapidly to give a uniform mass which commences to harden in a few minutes and is usually set within ten minutes of mixing.

In addition to the other parameters mentioned above, the rate of hardening and strength of final product, are determined by the powder/liquid ratio which is preferably as high as possible compatible with adequate working time. The optimum ratio for a particular powder and liquid may be determined readily with preliminary experiments. Too little or too much powder normally results in a mixture that is more difficult to form into a desired shape. Particularly good results have been obtained with powder/liquid ratios in the range 1.5 to 4:1. Careful matching of the powder and liquid components will enable an acceptable plastic mass to be obtained which will harden in an acceptable time.

The poly(carboxylic acid) which is used in the invention may be prepared by any of the customarily used polymerisation techniques. For example, polymerisation may be carried out in aqueous solution in the presence of a free radical initiator, for example ammonium persulphate and various chain transfer agents, for example isopropyl alcohol to give solutions containing up to about 30% by weight of the polymer. Such a solution may then be concentrated, if necessary, to give a more viscous solution, or either freeze dried, or air dried as a sheet or spray to give a solid particulate poly(carboxylic acid). In addition to traditional dental uses, the poly(- carboxylate) cements of the present invention may also find application in preventive dentistry, for example their adhesive properties may permit their use as pit and fissure sealants, and as fillers for cervical lesions.

The use of the poly(carboxylate) cement of the invention is not limited to dentistry and it may, for example, find application in other forms of surgery, particularly orthopaedic surgery, where it may be used to assist in the resetting of fractured bone material.

The invention is illustrated in the following Examples:

EXAMPLE 1

This example describes the production of a poly(carboxylate) dental cement from a fluoroaluminosilicate glass powder, and an aqueous solution of poly(acrylic acid) containing tartaric acid as a chelating agent.

The fluoroaluminosilicate glass powder is made as described in British ppatent application No. 61041/69, now British Pat. No. 1,316,129, by mixing together 175 parts by weight of silica, 100 parts by weight of alumina, 30 parts by weight of cryolite, 207 parts by weight of calcium fluoride, 32 parts by weight of aluminium fluoride, and 60 parts by weight of aluminium phosphate, and heating to a temperature of 1150° C. The glass is ground to a mesh size of 350 BSS mesh. The aqueous poly(acrylic acid) solution contains 50% by weight of a poly(acrylic acid) or average molecular weight 28,000 and 5% based on the weight of the poly(acrylic acid) of tartaric acid. The powder and the liquid are mixed together in the ratio of 3.5 gms. of powder to 1 milliliter of liquid. Hardness of the cement is measured by indentation 9 minutes after mixing. For comparison a sample of the powder is mixed with an identical poly(acrylic acid) solution except that the tartaric acid is omitted, in a power to liquid ratio of 3 gms. of powder to 1 milliliter of liquid, giving a cement of the same consistency as the previous cement containing the chelating agent. The results of setting time, working time, and hardness of the two cements are given below:

| | With Tartaric acid | Without tartaric acid |
|---|---|---|
| Setting time (min) | 3¼ | 6 |
| Working time (min) | 2 | 2½ |
| Wallace Indentation Number at 9 mins. | 120 | 600 |

EXAMPLE 2

This example describes the production of a poly(carboxylate) dental cement using a fluoroaluminosilicate glass powder and an aqueous solution of poly(acrylic acid) containing citric acid as a chelating agent.

The procedure of Example 1 is repeated except that the tartaric acid is replaced by 5% by weight of the poly(acrylic acid) of citric acid. The results of this cement are given below:

| | |
|---|---|
| Setting time | 3¾ mins |
| Working time | 2 mins |
| Wallace Indentation Number at 9 mins | 347 |

EXAMPLE 3

This example describes the production of a poly(carboxylate) dental cement using a fluoroaluminosilicate glass powder and an aqueous solution of poly(acrylic acid) containing tartaric acid as a chelating agent and propan-2-ol as a stabilising agent.

The procedure of Example 1 is repeated except that the liquid contains in addition to the tartaric acid, 5%, based on the weight of the poly(acrylic acid) of propan-2-ol. The results for this cement are given below:

| | |
|---|---|
| Setting time (min) | 3½ |
| Working time (min) | 2 |
| Wallace Indentation Number 9 mins | 120 |

We claim:
1. A process for the production of a poly(carboxylate) cement which comprises mixing a water soluble poly(carboxylic acid) having a relative viscosity of from 1.05 to 2.00 measured with a capillary viscometer of a 1% by weight to volume solution of the poly(carboxylic acid) in twice molar sodium hydroxide solution at 25° C. relative to the viscosity of the twice molar sodium hydroxide solution with an ion leachable glass cement powder in the presence of a water soluble chelating agent selected from the group consisting of compounds containing both chelating hydroxyl and carboxyl groups and metal chelates, and water to give a plastic mass which rapidly hardens to form a poly(carboxylate) cement, the amount of the chelating agent being at least 0.01% by weight based on the weight of the poly(carboxylic acid) and sufficient to improve the rate of hardening of the cement, as compared to the rate of hardening of the cement in the absence of said compound.

2. A process according to claim 1, in which the poly(carboxylic acid) is in the form of an aqueous solution containing from 20 to 65% by weight of the poly(carboxylic acid).

3. A process according to claim 2 in which the powder/liquid ratio is in the range of 0.5:1 to 5:1.

4. A process according to claim 1 in which the chelating agent is tartaric acid or citric acid.

5. A process according to claim 2 in which the chelating agent is a di- or tri-valent metal chelate.

6. A process according to claim 1, in which the poly(carboxylic acid) is a homopolymer of acrylic acid or a copolymer of acrylic acid and at least one comonomer selected from the group consisting of 2-chloroacrylic acid, 3-chloroacrylic acid, 2-bromoacrylic acid, 3-bromoacrylic acid, methacrylic acid, itaconic acid, maleic aid, glutaconic acid, aconitic acid, citraconic acid, mesaconic acid, fumaric acid, tiglicinic acid, acrylamide, acrylonitrile, vinyl chloride, allyl chloride, vinyl acetate and 2-hydroxymethyl methacrylate.

7. A process according to claim 1 in which the cement powder is selected from the group consisting of aluminosilicate glass powders and fluoroaluminosilicate glass powders.

8. A cement composition consisting essentially of an intimately blended mixture of an ion-leachable surgically acceptable glass cement powder, a water soluble poly(carboxylic acid) having a relative viscosity of from 1.05 to 2.00 measured with a capillary viscometer of a 1% by weight to volume solution of the poly(carboxylic acid) in twice molar sodium hydroxide solution at 25° C. relative to the viscosity of the twice molar sodium hydroxide solution and a water-soluble chelating agent selected from the group consisting of compounds containing both chelating hydroxyl and carboxyl groups and metal chelates, the ratio of cement powder to poly(carboxylic acid) being from 1:1 to 10:1, and said chelating agent being present in an amount of at least 0.01% by weight based on the weight of the poly(carboxylic acid) and sufficient to increase the rate of hardening of the cement as compared to the rate of hardening of the cement in the absence of said chelating agent, said cement composition being characterized by forming a poly(carboxylate) cement upon the addition of water thereto.

9. The cement composition according to claim 8, in which the chelating agent is tartaric acid or citric acid.

10. The cement composition according to claim 8, in which the chelating agent is a di- or tri-valent metal chelate.

11. The cement composition according to claim 8, in which the poly(carboxylic acid) is a homopolymer of acrylic acid or copolymer of acrylic acid and at least one comonomer selected from the group consisting of 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, tiglicinic acid, acrylamide, acrylonitrile, vinyl chloride, allyl chloride, vinyl acetate and 2-hydroxyethyl methacrylate.

12. The cement composition according to claim 8, in which the cement powder is selected from the group consisting of aluminosilicate glass powders and fluoroaluminosilicate glass powders.

13. The cement composition according to claim 8, wherein said chelating agent is tartaric acid.

14. The cement composition according to claim 8, wherein said chelating agent is selected from the group consisting of salicylic acid, citric acid, 2,4- and 2,6-dihydroxybenzoic acids, dihydroxy tartaric acid, tartaric acid, and complexes of $\beta$-diketones with aluminum and chromium.

15. The cement composition according to claim 8, wherein said glass powder is an aluminosilicate glass powder.

16. The cement composition according to claim 13, wherein said glass powder is a fluoroaluminosilicate glass powder.

17. A hardened poly(carboxylate) cement, particularly for dental purposes, which has been prepared by the process consisting essentially of mixing a water soluble poly(carboxylic acid) having a relative viscosity of from 1.05 to 2.00 measured with a capillary viscometer of a 1% by weight to volume solution of the poly(carboxylic acid) in twice molar sodium hydroxide solution at 25° C. relative to the viscosity of the twice molar sodium hydroxide solution with an ion-leachable surgically acceptable glass cement powder in the presence of water and in the presence of a water soluble chelating agent selected from the group consisting of compounds containing both chelating hydroxyl and carboxyl groups and metal chelates, the chelating agent being present in an amount of at least 0.01% by weight based on the weight of the poly(carboxylic acid) and sufficient to improve the rate of hardening of the cement as compared to the rate of hardening of the cement in the absence of said chelating agent.

18. The cement according to claim 17, wherein the reaction mixture consists essentially of from 15 to 85% by weight of the cement powder, from 3 to 50% by weight of the poly(carboxylic acid) and from 5 to 70% by weight of water, based on the total weight of the composition, and from at least 0.01% by weight, based on the poly(carboxylic acid), of said chelating agent.

19. The cement according to claim 17, in which the chelating agent is tartaric acid or citric acid.

20. The cement according to claim 17, in which the chelating agent is a di- or tri-valent metal chelate.

21. The cement according to claim 17, in which the poly(carboxylic acid) is a homopolymer of acrylic acid or a copolymer of acrylic acid and at least one comonomer selected from the group consisting of 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, tiglicinic acid, acrylamide, acrylonitrile, vinyl chloride, allyl chloride, vinyl acetate and 2-hydroxyethyl methacrylate.

22. The cement according to claim 17, in which the cement powder is selected from the group consisting of aluminosilicate glass powders and fluoroaluminosilicate glass powders.

* * * * *